(12) United States Patent
Cohen

(10) Patent No.: US 9,265,595 B2
(45) Date of Patent: Feb. 23, 2016

(54) HERNIA REPAIR DEVICE AND METHOD

(71) Applicant: Covidien LP, Mansfield, MA (US)

(72) Inventor: Matthew D. Cohen, Berlin, CT (US)

(73) Assignee: Covidien LP, Mansfield, MA (US)

( * ) Notice: Subject to any disclaimer, the term of this patent is extended or adjusted under 35 U.S.C. 154(b) by 86 days.

(21) Appl. No.: 14/345,801

(22) PCT Filed: Oct. 1, 2012

(86) PCT No.: PCT/US2012/058241
§ 371 (c)(1),
(2) Date: Mar. 19, 2014

(87) PCT Pub. No.: WO2013/049791
PCT Pub. Date: Apr. 4, 2013

(65) Prior Publication Data
US 2014/0221736 A1    Aug. 7, 2014

Related U.S. Application Data

(60) Provisional application No. 61/541,591, filed on Sep. 30, 2011.

(51) Int. Cl.
*A61F 13/00* (2006.01)
*A61F 2/00* (2006.01)
*A61B 17/00* (2006.01)
*A61B 17/02* (2006.01)
*A61B 17/04* (2006.01)

(52) U.S. Cl.
CPC ........... *A61F 2/0063* (2013.01); *A61B 17/0057* (2013.01); *A61B 17/02* (2013.01); *A61B 17/04* (2013.01); *A61B 2017/00597* (2013.01); *A61B 2017/00623* (2013.01); *A61B 2017/0496* (2013.01); *A61F 2002/0072* (2013.01)

(58) Field of Classification Search
CPC ................ A61F 2/0004; A61F 2/0063; A61F 2002/0068; A61F 2002/0072
USPC .......................... 600/29–32, 37; 128/DIG. 25
See application file for complete search history.

(56) References Cited

U.S. PATENT DOCUMENTS

| | | |
|---|---|---|
| 5,116,357 A | 5/1992 | Eberbach |
| 5,405,360 A | 4/1995 | Tovey |
| 5,634,931 A | 6/1997 | Kugel |
| 2008/0188874 A1 | 8/2008 | Henderson |
| 2009/0156986 A1 | 6/2009 | Trenhaile |

(Continued)

OTHER PUBLICATIONS

Supplementary European Search Report from corresponding EP12836720 dated Jun. 2, 2015.

(Continued)

*Primary Examiner* — John Lacyk

(57) ABSTRACT

A hernia repair device includes a surgical mesh configured to extend across a tissue defect and a plurality of filament loops coupled to the surgical mesh toward an outer periphery thereof. A tissue retracting member is slidably disposed about each of the filament loops. Each tissue retracting member is configured for slidable movement about the filament loop between a first position, wherein the tissue retracting member is spaced-apart from the surgical mesh, and a second position, wherein the tissue retracting member is positioned adjacent the surgical mesh to facilitate the retraction of tissue surrounding the tissue defect.

21 Claims, 4 Drawing Sheets

(56) References Cited

U.S. PATENT DOCUMENTS

2009/0171142 A1 7/2009 Chu
2010/0069930 A1 3/2010 Roslin et al.

OTHER PUBLICATIONS

International Search Report for PCT/US12/58241 date of completion is Jan. 28, 2013 (3 pages).
Chinese Office Action dated Oct. 12, 2015 in corresponding Chinese Patent Application No. 201280047943.9.

HERNIA REPAIR DEVICE AND METHOD

CROSS-REFERENCE TO RELATED APPLICATIONS

This application is a National Stage Application of PCT/US12/58241 under 35USC §371 (a), which claims priority of U.S. Provisional Patent Application Ser. No. 61/541,591 filed Sep. 30, 2011, the disclosures of each of the above-identified applications are hereby incorporated by reference in their entirety.

BACKGROUND

1. Technical Field

The present disclosure relates to hernia repair devices and, more particularly, to surgical mesh prosthetics for use in hernia repair.

2. Background of Related Art

Wound closure devices, such as sutures, filaments, and staples, as well as other repair devices, such as mesh or patch reinforcements, are frequently used to repair tissue defects, e.g., herniated tissue, and other damaged and/or diseased tissue. For example, in the case of hernias, a surgical mesh or patch is commonly used to reinforce the abdominal wall. The surgical mesh is generally sized to extend across the defect and is adapted to flex or bend in order to conform to the abdominal wall. The surgical mesh is typically held in place by adhering, suturing or stapling the mesh to the surrounding tissue.

However, difficulties may arise during the course of a hernia repair procedure, particularly with regard to securely affixing the mesh to surrounding tissue. These difficulties are often attributed to anatomical spatial constrains and/or reduced, or limited, access to the surgical site. Improper or faulty affixing of the mesh may result in re-herniation, dislodging or repositioning of the surgical mesh relative to tissue and/or may allow viscera to enter the defect.

U.S. Pat. No. 7,828,854 discloses an implantable repair device formed from multiple structures including a patch member, reinforcing elements, and a pair of looped elements extending therefrom. The looped elements include sutures (or other grasping elements) inserted therethrough. In use, the implantable repair device is inserted into a tissue defect and the sutures are pulled to position the implantable repair device against the tissue. The looped portions are then secured to tissue to fix the implantable repair device in position.

SUMMARY

In accordance with one embodiment of the present disclosure, a hernia repair device is provided. The hernia repair device includes a surgical mesh configured to extend across a tissue defect and a plurality of filament loops coupled to the surgical mesh in proximity of an outer periphery thereof. A tissue retracting member is slidably disposed about each of the filament loops. Each of the tissue retracting members is configured for slidable movement about the filament loop between a first position, wherein the tissue retracting member is spaced-apart from the surgical mesh, and a second position, wherein the tissue retracting member is positioned adjacent the surgical mesh to facilitate the retraction of tissue surrounding the tissue defect.

In one embodiment, the hernia repair device further includes a plurality of tissue retracting flaps. Each flap is coupled to the surgical mesh in proximity of an outer periphery of the surgical mesh at a fixed end thereof and extends inwardly therefrom to a free end. Each flap is moveable about the fixed end thereof between a first position, wherein the flaps are substantially co-planar with the surgical mesh, and a second position, wherein the flaps extend from the surgical mesh to retract tissue surrounding the tissue defect. In such an embodiment, one of the filament loops may be coupled to each of the tissue retracting flaps.

In another embodiment, each of the tissue retracting flaps defines a generally triangular-shaped configuration having an apex at the free end thereof. In this embodiment, the filament loops may be coupled to the flaps toward the apexes thereof. Further, the flaps may be formed from surgical mesh.

In yet another embodiment, a resiliently deformable support assembly, e.g., formed from a plurality of support members, is coupled to the surgical mesh and is configured to provide structural support to the surgical mesh. More specifically, the surgical mesh may define a substantially circular configuration and the support assembly may be annularly disposed about the surgical mesh in proximity of the outer periphery thereof. Further, the support assembly may define a serpentine-shaped configuration along the length thereof.

In still another embodiment, the tissue retracting member includes first and second spaced-apart lumens extending therethrough. Each of the lumens is configured to slidably receive a portion of the filament loop therethrough.

In still yet another embodiment, the tissue retracting member includes a fixation window defined therethrough. The fixation window is configured to facilitate securing of the surgical mesh to the distal surface of tissue surrounding the tissue defect.

A method of repairing a tissue defect is also provided in accordance with the present disclosure. The method includes providing a hernia repair device according to any of the embodiments discussed above, positioning the hernia repair device within a tissue defect such that the surgical mesh extends across the tissue defect, sliding the tissue retracting members distally along the filament loops to a position adjacent the surgical mesh, and pulling the filament loops proximally to retract tissue adjacent the tissue defect.

In one embodiment, the method further includes securing the surgical mesh to a distal surface of the retracted tissue. The fixation window of each of the tissue retracting members may be used to facilitate positioning and securing of the surgical mesh to the distal surface of tissue surrounding the tissue defect.

In another embodiment, the method further includes sliding the tissue retracting members proximally along the filament loops and decoupling the filament loops from the surgical mesh.

In yet another embodiment, the support assembly is resiliently deformed to facilitate positioning of the hernia repair device within the tissue defect.

BRIEF DESCRIPTION OF THE DRAWINGS

Various embodiments of the present disclosure are described herein with reference to the drawings wherein.

DETAILED DESCRIPTION

Figure 1:
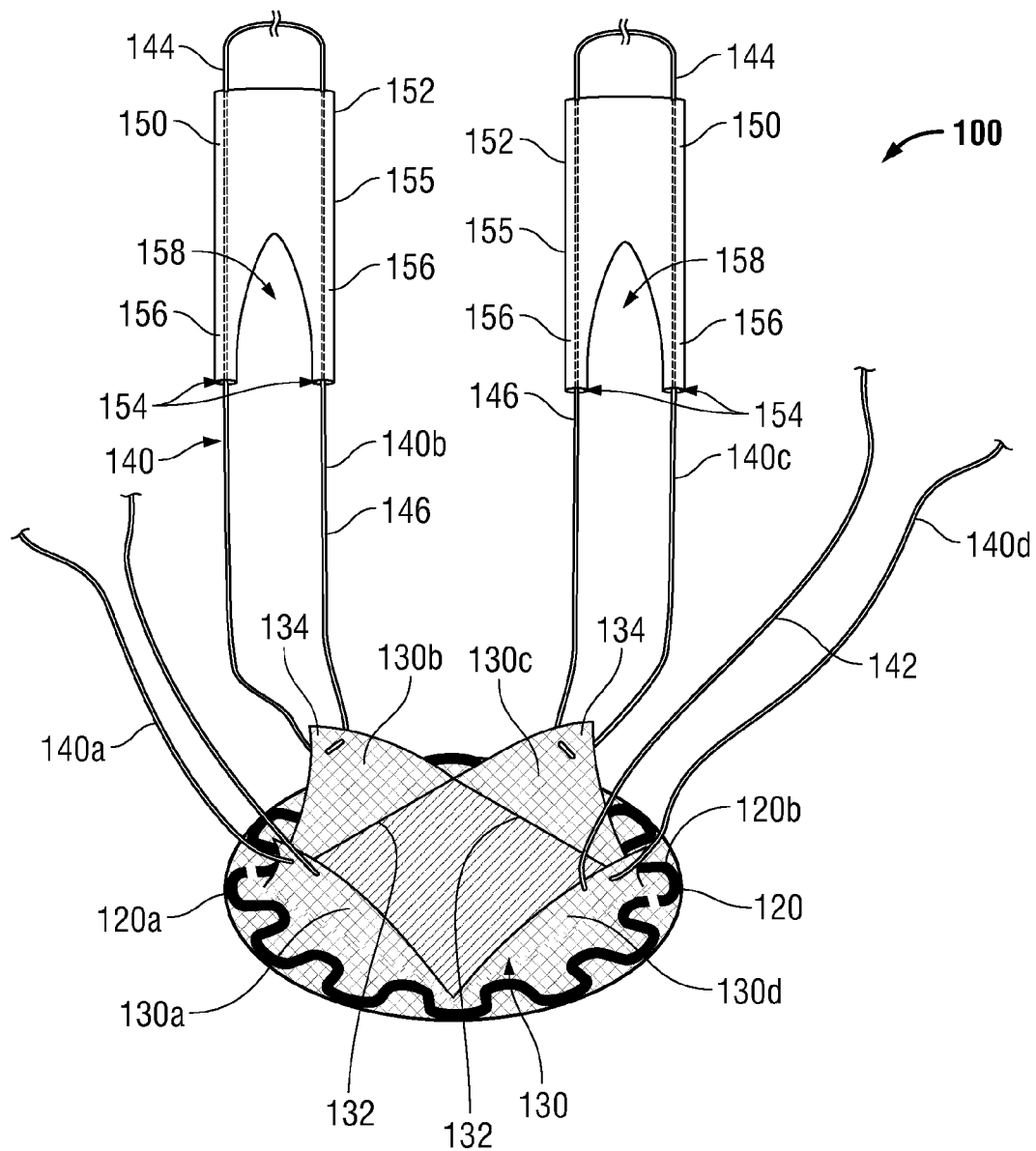
FIG. 1 is a top, perspective view of one embodiment of a hernia repair device provided in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
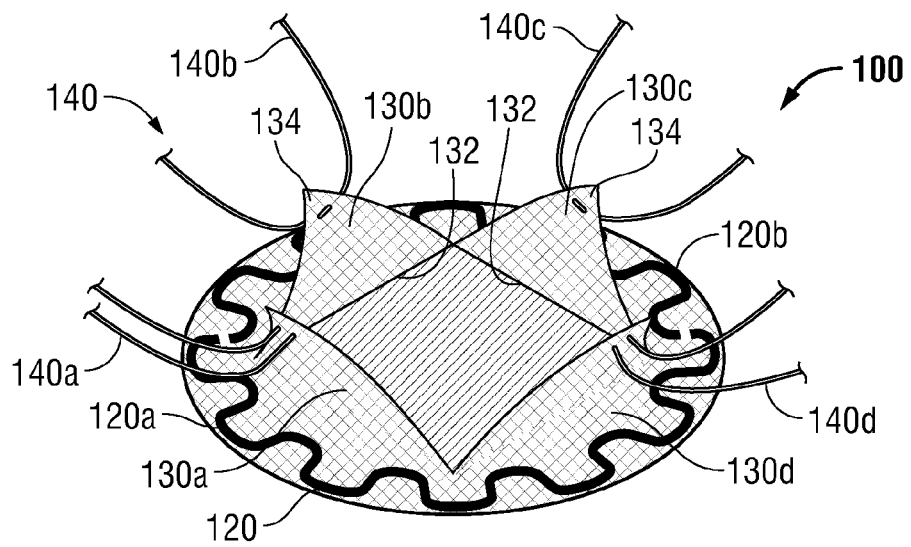
FIG. 2 is a top view of the hernia repair device of FIG. 1.
Figure 3:
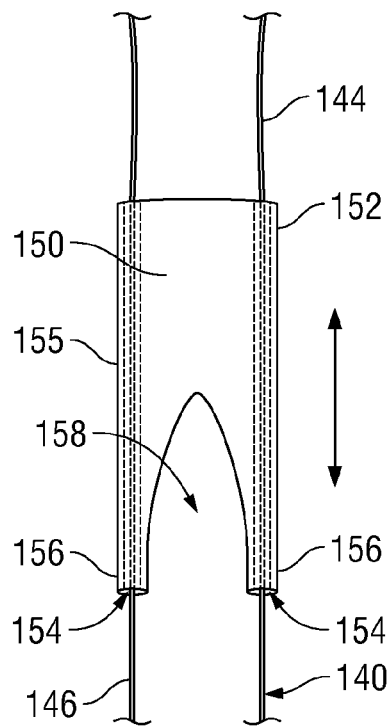
FIG. 3 is a side view of a retracting member of the hernia repair device of FIG. 1.
Figure 4:
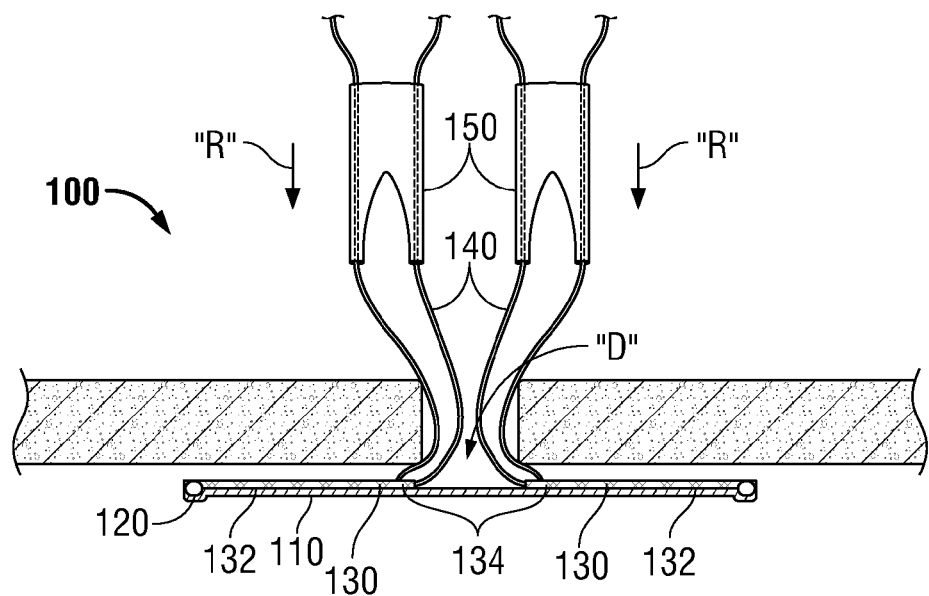
FIG. 4 is a longitudinal, cross-sectional view of the hernia repair device of FIG. 1 positioned within a tissue defect wherein the retracting members are disposed in a first position.
Figure 5:
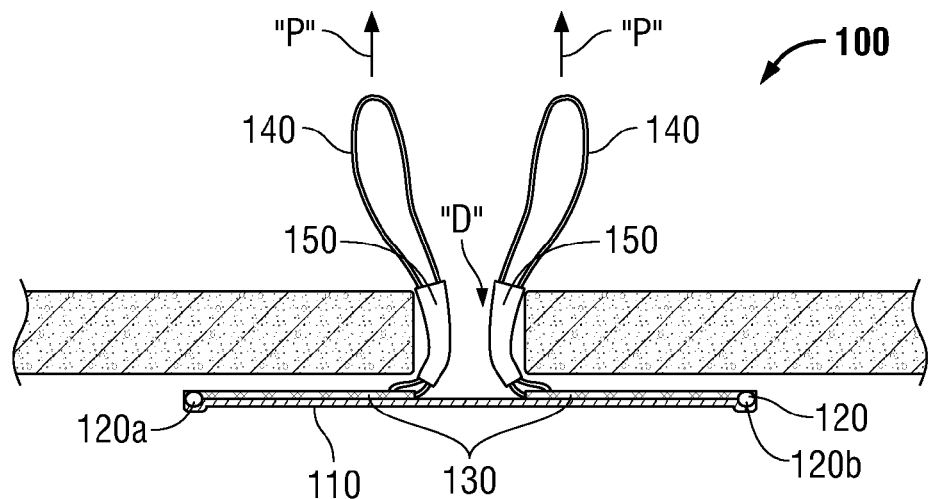
FIG. 5 is a longitudinal, cross-sectional view of the hernia repair device of FIG. 1 positioned within the tissue defect wherein the retracting members are disposed in a second position.
Figure 6:
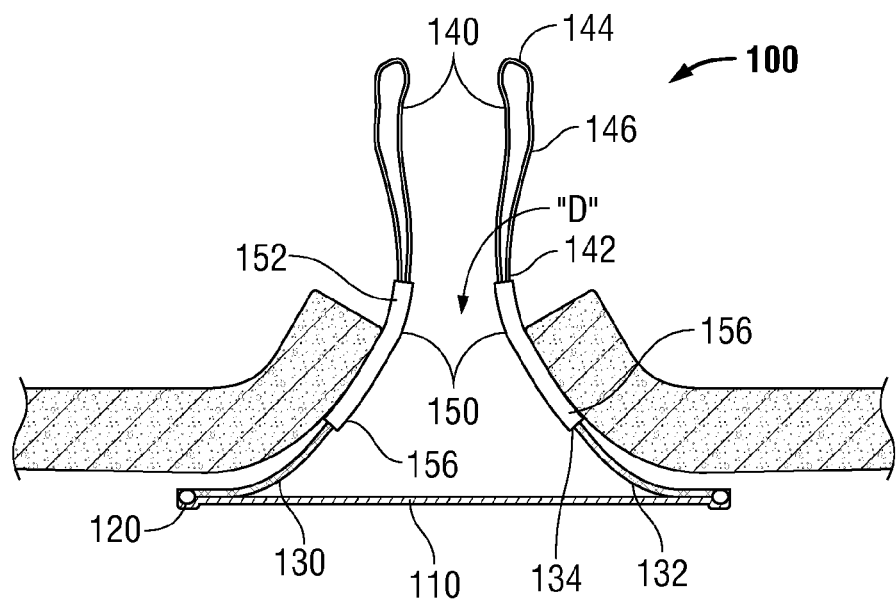
FIG. 6 is a longitudinal, cross-sectional view of the hernia repair device of FIG. 1 retracting tissue surrounding the tissue defect.

Referring now to FIGS. 1-3, one embodiment of a hernia repair device provided in accordance with the present disclosure is shown generally identified by reference numeral 100. Hernia repair device 100 includes a surgical mesh 110 configured for insertion into a tissue defect "D" (see FIGS. 4-6). Surgical mesh 110 defines a generally flat, circular configuration (although other configurations are contemplated) and is dimensioned to extend across the tissue defect "D" (FIGS. 4-6). It is envisioned that mesh 110 be flexible to conform to the anatomy of the defect "D" (FIGS. 4-6) and tissue surrounding the defect "D" (FIGS. 4-6). Mesh 110 may be formed from any suitable biomaterial, e.g., synthetic biomaterials or natural materials, including bioabsorbable and biodegradable materials.

Mesh 110 may also include at least one bioactive agent. The term "bioactive agent", as used herein, is used in its broadest sense and includes any substance or mixture of substances that have clinical use. A bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. For example, surgical mesh 110 may be coated with an anti-adhesive, e.g., on a distal surface thereof, to inhibit adhesion of mesh 110 to tissue and/or with a local anesthetic for temporary pain relief during implantation. It is envisioned that the bioactive agent may be applied to surgical mesh 110 in any suitable form of matter, e.g., films, powders, liquids, gels, combinations thereof, and the like.

With continued reference to FIGS. 1-3, hernia repair device 100 includes a pair of support members 120a, 120b (collectively support assembly 120) coupled to surgical mesh 110. Support assembly 120 is formed from two support members 120a, 120b (although greater or fewer than two support members 120a, 120b are contemplated), as best shown in FIG. 2, that cooperate to define the generally annular-shaped support assembly 120. Support assembly 120 may be disposed on a proximal surface of mesh 110 toward an outer periphery thereof, e.g., annularly about the circular mesh 110, and may be engaged to mesh 110 in any suitable fashion, e.g., adhering, welding, etc. Support assembly 120 is configured to provide structural support to surgical mesh 110, while also permitting surgical mesh 110 to being inserted into and positioned within the tissue defect "D" (FIGS. 4-6). As such, support assembly 120 may be formed from a resiliently flexible material, or any other suitable flexible, or semi-rigid material. Further, as shown in FIGS. 1 and 2, support assembly 120 may be generally annular in shape and may define a serpentine configuration along the length thereof, although other configurations are contemplated. Additionally, support members 120a, 120b of support assembly 120 may be engaged to one another, e.g., to form a continuous support assembly 120, or, as shown in the Figures, may define a plurality of gaps, e.g., two (2) gaps, therebetween.

Referring now to FIGS. 1 and 2, hernia repair device 100 includes a plurality of tissue retracting flaps 130 coupled to mesh 110, e.g., four (4) tissue retracting flaps 130a-d. Each tissue retracting flap 130 includes a fixed end 132 engaged to mesh 110 toward an outer periphery thereof, e.g., via adhering, welding, stitching, etc. Tissue retracting flaps 130 extend inwardly from the outer periphery of mesh 110 to free ends 134. More specifically, tissue retracting flaps 130 may define substantially triangular-shaped configurations wherein the base constitutes fixed end 132 and wherein the apex constitutes free end 134. Tissue retracting flaps 130 may be formed from any suitable material including surgical mesh materials, e.g., synthetic biomaterials or natural materials, including bioabsorbable and biodegradable materials. As will be described in greater detail below, tissue retracting flaps 130 are moveable relative to surgical mesh 110 between a first position, wherein tissue retracting flaps 130 are substantially co-planar with mesh 110 (see FIG. 5), and a second position, wherein tissue retracting flaps 130 extend proximally from mesh 110 (see FIG. 6).

Still referring to FIGS. 1 and 2, a loop of filament 140, e.g., suture, threading, wire, etc., is coupled to each of the tissue retracting flaps 130a-d toward the free ends 134 thereof. More specifically, each filament loop 140a-d is disposed through a corresponding tissue retracting flap 130a-d, e.g., through the mesh, in embodiments where tissue retracting flaps 130 are formed from a surgical mesh material, at a first end 142 thereof and extends therefrom to second end 144. An intermediate segment 146 interconnects the first and second ends 142, 144, respectively, of filament loops 140a-140d. Alternatively, filament loops 140 may be secured to tissue retracting flaps 130 in any other suitable fashion. It is also envisioned that multiple filament loops 140 are secured to each tissue retracting flap 130 or that one filament loop 140 is secured to multiple tissue retracting flaps 130.

Referring now to FIGS. 1 and 3, each filament loop 140 includes a tissue retracting member 150 slidably disposed thereon. More specifically, each tissue retracting member 150 includes a base 152 and a pair of lumens 154 extending therethrough. Each lumen 154 is configured to slidably receive a length of filament loop 140 therethrough such that tissue retracting member 150 may be slid along filament loop 140 from a position spaced-apart from the tissue retracting flap 130 (see FIG. 4), e.g., at the second end 144 of filament loop 140, to a position adjacent tissue retracting flap 130 (see FIG. 5), e.g., at the first end 142 of filament loop 140. Base 152 of tissue retracting member 150 may be formed from any suitable biocompatible material, e.g., a polymer, and be substantially rigid, semi-rigid, or flexible in configuration.

Tissue retracting member 150, as best shown in FIG. 3, further includes a pair of fingers 156 that extend from a distal end 155 thereof. Each lumen 154 extends through one of the fingers 156. Thus, as can be appreciated, filament loop 140 is configured to extend through base 152 and both of the fingers 156 of tissue retracting member 150. Further, a fixation window 158 is defined between fingers 156 to facilitate, as will be described in greater detail, securing of tissue retracting flaps 130 (see FIGS. 1-2) to a distal surface of tissue surrounding the tissue defect "D" (FIGS. 4-6).

Turning now to FIGS. 4-7, the use and operation of hernia repair device 100 will be described. Initially, hernia repair device 100 is inserted through the tissue defect "D" to a distal side of the tissue defect "D." Due to the flexible configuration of surgical mesh 110 and the resiliently flexible configuration of support assembly 120, hernia repair device 100 may be folded, rolled, bent, or otherwise manipulated to facilitate passage through the tissue defect "D" with minimal trauma to surrounding tissue. Once inserted through the tissue defect "D," as shown in FIGS. 4-5, hernia repair device 100 is oriented such that support assembly 120 is substantially annularly disposed about the tissue defect "D" with tissue retracting flaps 130 positioned adjacent the distal surface of tissue. At this point, as shown in FIG. 5, tissue retracting flaps 130 remain disposed in the first position, wherein tissue retracting flaps 130 are substantially co-planar with mesh 110. Further, in this position, free ends 134 of tissue retracting flaps 130 are positioned adjacent to and distal of the tissue defect "D," thus allowing filament loops 140 to extend proximally though the tissue defect "D."

With reference to FIGS. 4 and 5, once hernia repair device 100 is positioned as mentioned above, tissue retracting members 150 may be slid into position. More specifically, tissue retracting members 150, lead by fingers 156, are slid distally along and relative to filament loops 140 in the direction of arrows "R." As best shown in FIG. 5, tissue retracting members 150 are translated from the first position (FIG. 4) to the second position (FIG. 5), wherein tissue retracting members 150 are positioned adjacent tissue retracting flaps 130 and at least partially between mesh 110 and a distal surface of tissue surrounding the tissue defect "D."

As shown in FIG. 5, with tissue retracting members 150 in position adjacent tissue retracting flaps 130, hernia repair device 100 may be positioned and secured to tissue surrounding the tissue defect "D." In order to position hernia repair device 100, the clinician grasps filament loops 140 and pulls proximally, in the direction of arrows "P," such that tissue retracting flaps 130 and, ultimately, mesh 110 and support assembly 120, are pulled proximally to move mesh 110 into approximation with the distal surface of tissue surrounding the tissue defect "D" and to automatically center mesh 110 relative to the tissue defect "D."

Figure 7:
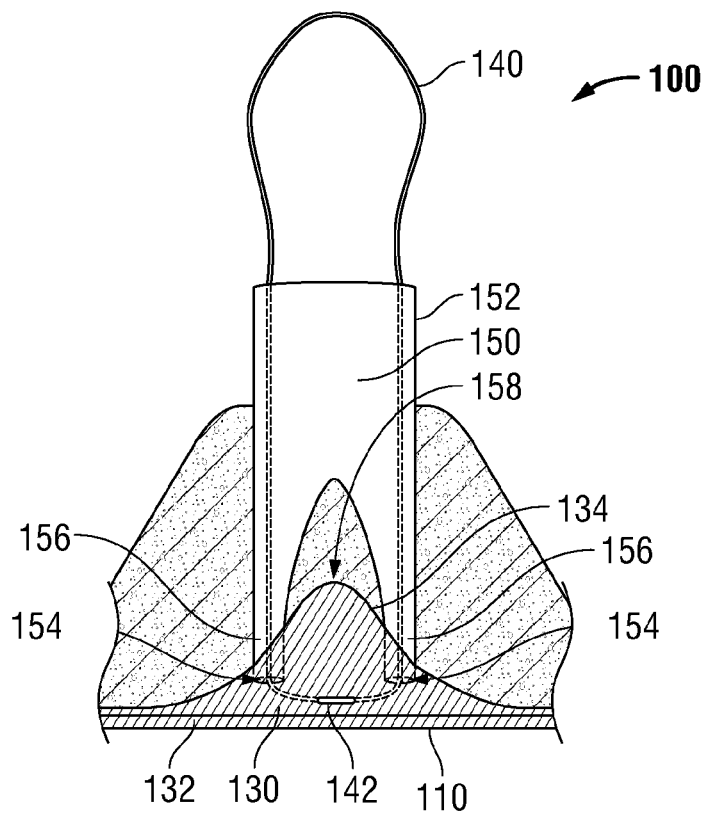
FIG. 7 is a transverse, cross-sectional view of the hernia repair device of FIG. 1 retracting tissue surrounding the tissue defect.

With continued reference to FIG. 5, in conjunction with FIGS. 6 and 7, further proximal pulling of filament loops 140 effects movement of tissue retracting flaps 130 from the first, substantially co-planar position relative to mesh 110 to the second, extended position relative to mesh 110, while mesh 110 is maintained in an approximated position adjacent the distal surface of tissue surrounding the tissue defect"D" by support assembly 120. As tissue retracting flaps 130 are pulled toward the extended position, tissue adjacent the tissue defect "D" is retracted upwardly and outwardly to expose at least a portion of the distal surface of tissue. Tissue retracting members 150, which, as mentioned above, are positioned adjacent tissue retracting flaps 130, are likewise moved upwardly and outwardly as filament loops 140 are pulled proximally to facilitate the retraction of tissue surrounding the tissue defect "D."

As best shown in FIG. 7, with the distal surface of tissue at least partially exposed, the clinician may secure tissue retracting flaps 130 to the distal surface of tissue in any suitable fashion, e.g., adhering, tacking, suturing, etc. As mentioned above, in the second position, tissue retracting members 150 are positioned adjacent tissue retracting flaps 130. More particularly, fingers 156 of tissue retracting members 150 are positioned adjacent the respective tissue retracting flaps 130. As can be appreciated, in this position, fixation window 158 provides an opening to provide the clinician with better visualization at the fixation point and through which surgical instrumentation (not shown) for securing tissue retracting flaps 130 to the distal surface of tissue may be inserted. Further, fixation window 158 also serves as a guide for securing tissue retracting flaps 130 to tissue, helping to ensure that tissue retracting flaps 130 are secured to tissue at an appropriate position to maintain mesh 110 in position during the healing process.

Thereafter, once hernia repair device 100 has been secured to the distal surface of tissue surrounding the tissue defect "D," the clinician may translate tissue retracting members 150 proximally from the second position back to the first position (see FIG. 4) and release filament loops 140, allowing tissue retracting flaps 130 to return to the first position under the urging of tissue surrounding the tissue defect "D" back to an at-rest, or un-retracted position. Thereafter, filament loops 140 may be removed, e.g., cut-off, from tissue retracting flaps 130, leaving mesh 110 secured within the tissue defect "D."

Hernia repair devices of the present disclosure include a surgical mesh configured to extend across a tissue defect, a plurality of filament loops coupled to the surgical mesh in proximity of an outer periphery thereof, and a tissue retracting member slidably disposed about each of the filament loops. Each of the tissue retracting flaps is configured for slidable movement about the filament loop between a first position, wherein the tissue retracting member is spaced-apart from the surgical mesh, and a second position, wherein the tissue retracting member is positioned adjacent the surgical mesh to facilitate the retraction of tissue surrounding the tissue defect.

In any of the presently disclosed embodiments, a plurality of tissue retracting flaps is coupled to the surgical mesh in proximity of an outer periphery of the surgical mesh. The flaps are coupled to the surgical mesh at fixed ends thereof and extend inwardly therefrom to free ends thereof. Each flap is moveable about the fixed end thereof between a first position, wherein the flaps are substantially co-planar with the surgical mesh, and a second position, wherein the flaps extend from the surgical mesh to retract tissue surrounding the tissue defect. A filament loop may be coupled to each of the tissue retracting flaps. Each flap may define a generally triangular-shaped configuration having an apex at the free end thereof such that the filament loop may be coupled to the flaps toward the apexes thereof. Further, in any embodiment, the flaps may be formed from surgical mesh.

In any of the presently disclosed embodiments, a resiliently deformable support assembly may be coupled to the surgical mesh to provide structural support to the surgical mesh. In fact, the surgical mesh may define a substantially circular configuration such that the support assembly may be annularly disposed about the surgical mesh in proximity of the outer periphery of the surgical mesh. The support member may also define a serpentine-shaped configuration along at least a portion of a length thereof.

In any of the presently disclosed embodiments, the tissue retracting member includes first and second spaced-apart lumens extending therethrough. Each of the first and second lumens configured to slidably receive a portion of the filament loop therethrough. The tissue retracting member may also include a fixation window defined therethrough, the fixation window configured to facilitate securing of the surgical mesh to the distal surface of tissue surrounding the tissue defect.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A hernia repair device, comprising:
   a surgical mesh configured to extend across a tissue defect;
   a plurality of filament loops coupled to the surgical mesh in proximity of an outer periphery thereof; and
   a tissue retracting member slidably disposed about each of the filament loops, each tissue retracting member slidable along the filament loop between a first position, wherein the tissue retracting member is spaced-apart from the surgical mesh, and a second position, wherein the tissue retracting member is positioned adjacent the surgical mesh to facilitate the retraction of tissue surrounding the tissue defect.

2. The hernia repair device according to claim 1, further comprising a plurality of tissue retracting flaps, each flap coupled to the surgical mesh in proximity of an outer periphery of the surgical mesh at a fixed end thereof and extending inwardly therefrom to a free end, each flap moveable about the fixed end thereof between a first position, wherein the flaps are substantially co-planar with the surgical mesh, and a second position, wherein the flaps extend from the surgical mesh to retract tissue surrounding the tissue defect.

3. The hernia repair device according to claim 2, wherein one filament loops is coupled to each of the tissue retracting flaps.

4. The hernia repair device according to claim 3, wherein each flap defines a generally triangular-shaped configuration having an apex at the free end thereof and wherein the filament loops are coupled to the flaps toward the apexes thereof.

5. The hernia repair device according to claim 2, wherein the flaps are formed from surgical mesh.

6. The hernia repair device according to claim 1, further comprising a resiliently deformable support assembly coupled to the surgical mesh and configured to provide structural support to the surgical mesh.

7. The hernia repair device according to claim 6, wherein the surgical mesh defines a substantially circular configuration and wherein the support assembly is annularly disposed about the surgical mesh in proximity of the outer periphery of the surgical mesh.

8. The hernia repair device according to claim 6, wherein the support assembly defines a serpentine-shaped configuration along at least a portion of a length thereof.

9. The hernia repair device according to claim 1, wherein the tissue retracting member includes first and second spaced-apart lumens configured to slidably receive a portion of the filament loop therethrough.

10. The hernia repair device according to claim 1, wherein the tissue retracting member includes a fixation window defined therethrough, the fixation window configured to facilitate securing of the surgical mesh to the distal surface of tissue surrounding the tissue defect.

11. A method of repairing a tissue defect, the method comprising the steps of:
    providing a hernia repair device including:
        a surgical mesh;
        a plurality of filament loops coupled to the surgical mesh in proximity of an outer periphery thereof; and
        a tissue retracting member slidably disposed about each of the filament loops;
    positioning the hernia repair device within a tissue defect such that the surgical mesh extends across the tissue defect;
    sliding the tissue retracting members distally along the filament loops to a position adjacent the surgical mesh; and
    pulling the filament loops proximally to retract tissue adjacent the tissue defect.

12. The method according to claim 11, further comprising the step of securing the surgical mesh to a distal surface of the retracted tissue.

13. The method according to claim 12, wherein each tissue retracting member includes a fixation window defined therethrough, the fixation window configured to facilitate securing of the surgical mesh to the distal surface of tissue surrounding the tissue defect.

14. The method according to claim 12, further comprising the steps of:
    sliding the tissue retracting members proximally along the filament loops; and
    decoupling the filament loops from the surgical mesh.

15. The method according to claim 11, wherein the hernia repair device further comprises a resiliently deformable support assembly coupled to the surgical mesh and configured to provided structural support to the surgical mesh.

16. The method according to claim 15, wherein the support assembly is resiliently deformed to facilitate positioning of the hernia repair device within the tissue defect.

17. The method according to claim 15, wherein the support assembly defines a serpentine-shaped configuration along at least a portion of a length thereof.

18. The method according to claim 15, wherein the tissue retracting member includes first and second spaced-apart lumens extending therethrough, each of the first and second lumens configured to slidably receive a portion of the filament loop therethrough.

19. The method according to claim 11, wherein the hernia repair device further includes a plurality of tissue retracting flaps, each flap coupled to the outer periphery of the surgical mesh at a fixed end thereof and extending inwardly therefrom to a free end, each flap movable about the fixed end thereof between a first position, wherein the flaps are substantially co-planar with the surgical mesh, and a second position, wherein the flaps extend from the surgical mesh to retract tissue surrounding the tissue defect.

20. The method according to claim 19, wherein one of the filament loops is coupled to each of the tissue retracting flaps.

21. The hernia repair device according to claim 9, wherein the tissue retracting member includes first and second spaced-apart finger members, each finger member including one of the first and second lumens.

* * * * *